United States Patent [19]

Prescher et al.

[11] 4,087,455

[45] May 2, 1978

[54] PROCESS FOR THE CONTINUOUS PREPARATION OF PERCARBOXYLIC ACIDS IN ORGANIC SOLUTIONS

[75] Inventors: Günter Prescher; Gerd Schreyer, both of Hanau; Helmut Waldmann; Wulf Schwerdtel, both of Leverkusen, all of Germany

[73] Assignees: Bayer Aktiengesellschaft, Leverkusen; Deutsche Gold-und Silber-Scheideanstalt Vormal Roessler, Frankfurt am Main, both of Germany

[21] Appl. No.: 678,824

[22] Filed: Apr. 28, 1976

[30] Foreign Application Priority Data

Apr. 30, 1975  Germany .............................. 2519295

[51] Int. Cl.$^2$ ............................................. C07C 179/10
[52] U.S. Cl. ................................. 260/502 R; 203/14; 203/DIG. 6; 203/DIG. 9
[58] Field of Search .................. 208/89; 260/502 R; 203/14, 98, 99; 423/584, 587, 588, 589

[56] References Cited

U.S. PATENT DOCUMENTS

| | | | |
|---|---|---|---|
| 2,741,584 | 10/1956 | Holmes et al. | 203/98 |
| 2,814,641 | 11/1957 | Phillips et al. | 260/502 R |
| 3,043,666 | 7/1962 | Siwinski | 423/589 |
| 3,284,491 | 11/1966 | Karoch et al. | 260/502 R |
| 3,341,297 | 9/1967 | MacLean et al. | 423/587 |
| 3,755,185 | 9/1973 | Waldmann | 423/584 |

FOREIGN PATENT DOCUMENTS

| | | | |
|---|---|---|---|
| 1,048,569 | 1/1959 | Germany | 260/502 R |
| 2,312,280 | 9/1974 | Germany | 260/502 R |
| 2,262,970 | 7/1974 | Germany | 260/502 R |

*Primary Examiner*—Bernard Helfin
*Assistant Examiner*—Werren B. Lone
*Attorney, Agent, or Firm*—Burgess, Dinklage & Sprung

[57] ABSTRACT

Process for the continuous preparation of organic solutions of percarboxylic acids by reaction of aqueous hydrogen peroxide with the corresponding carboxylic acid in the presence of an acid, water-soluble catalyst, extraction of the resulting reaction mixture with an organic solvent and recycle of the raffinate, containing hydrogen peroxide, after reconcentration by the removal of water by distillation into the reaction. The raffinate is fed, together with the whole of that amount of hydrogen peroxide which essentially to the consumption of hydrogen peroxide in the reaction or with a part thereof, into the distillation for the removal of water. The amount of water which essentially corresponds to the sum of the water of reaction formed during the reaction and the water introduced into the process with the feed products is distilled off under reduced pressure. The sump product, thus obtainable, from the distillation is recycled into the reaction.

28 Claims, No Drawings

PROCESS FOR THE CONTINUOUS PREPARATION OF PERCARBOXYLIC ACIDS IN ORGANIC SOLUTIONS

The following applications are related to the process hereof for production of propylene oxide as being directed to aspects of the process, some of which are disclosed herein.

| German Serial No. | U.S. Atty's. Docket No. | U.S. Serial No. |
|---|---|---|
| P 25 19 288.5 | Bayer 2883 | 678,819 |
| P 25 19 300.4 | Bayer 2884 | 678,820 |
| P 25 19 299.8 | Bayer 2885 | 678,821 |
| P 25 19 298.7-42 | Bayer 2886 | 678,822 |
| P 25 19 297.6 | Bayer 2887 | 678,823 |
| P 25 19 293.2-42 | Bayer 2889 | 678,825 |
| P 25 19 292.1-42 | Bayer 2890 | 678,826 |
| P 25 19 291.0-42 | Bayer 2891 | 678,827 |
| P 25 19 289.6 | Bayer 2892 | 678,828 |
| P 25 19 297.4 | Bayer 2893 | 678,829 |

All of the German applications were filed Apr. 30, 1975. Those applications are incorporated herein by reference.

The present invention relates to an improved continuous process for the preparation of organic solutions of percarboxylic acids.

Percarboxylic acids in organic solution are used to carry out selective oxidation reactions. For example, it is possible to convert olefines into olefine oxides using an organic solution of a percarboxylic acid as the epoxidising agent (D. Swern "Organic Peroxides", Wiley Interscience 1971, volume 2, page 355 – 413, especially page 360 et seq.).

As is known, organic solutions of aliphatic percarboxylic acids with up to 4 carbon atoms and of aromatic percarboxylic acids can be prepared by reaction of aqueous hydrogen peroxide with a carboxylic acid in the presence of an acid catalyst with subsequent extraction of the percarboxylic acid from the resulting reaction mixture (D. Swern, loc. cit., volume 1, page 313 to 497). In general, water-soluble, strongly acid compounds, especially sulphuric acid, are used as the acid catalyst. However, strong, water-soluble organic carboxylic acids or sulphonic acids, such as methanesulphonic acid, are also suitable (D. Swern, loc. cit., volume 1, page 317).

The reaction mixture which is obtained from the reaction of hydrogen peroxide and the carboxylic acid in the presence of a water-soluble acid catalyst always contains unreacted hydrogen peroxide, as can be seen from the equation which follows, in which RCOOH denotes a carboxylic acid and RCOOOH denotes a percarboxylic acid; the equation shows that the reaction is an equilibrium reaction.

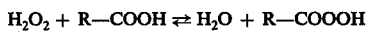

$$H_2O_2 + R-COOH \rightleftarrows H_2O + R-COOOH$$

If a reaction mixture, thus obtained, is now extracted in a known manner in order to isolate the percarboxylic acid, the unreacted hydrogen peroxide, in addition to the water-soluble acid catalyst, is obtained in the raffinate. As a rule, this raffinate has been discarded. However, processes for the preparation of organic solutions of percarboxylic acids have also been described in which the raffinate has been worked up in order to recycle all or part of the constituents contained therein into the reaction of hydrogen peroxide with the carboxylic acid.

The procedure according to the process of DOS (German Published Specification) No. 2,312,281 is such that unreacted hydrogen peroxide contained in the raffinate is destroyed and the acid catalyst is regenerated by reconcentration (DOS (German Published Specification) No. 2,312,281, page 5, 3rd paragraph).

In another process, according to DOS (German Published Specification) No. 2,262,970, both the unreacted hydrogen peroxide and the acid catalyst which are contained in the raffinate are recovered for the reaction of hydrogen peroxide with carboxylic acid by feeding the raffinate to an evaporator unit, in which the water introduced with the starting materials and formed by the reaction is distilled off over the top and the material withdrawn from the sump, which essentially contains the unreacted hydrogen peroxide and the acid catalyst, is recycled into the reaction of hydrogen peroxide with carboxylic acid. The $H_2O_2$ required to make up the hydrogen peroxide consumed in the reaction with carboxylic acid is added to the raffinate after reconcentration (DOS (German Published Specification) No. 2,262,970, page 2, third complete paragraph). The percarboxylic acid yields quoted for this process are from 87 to 90.5%, relative to hydrogen peroxide employed (DOS (German Published Specification) No. 2,262,970, example 1).

In contrast, a process has now been found for the continuous preparation of organic solutions of percarboxylic acids by reaction of aqueous hydrogen peroxide with the corresponding carboxylic acid in the presence of an acid, water-soluble catalyst, extraction of the resulting reaction mixture with an organic solvent and recycle of the raffinate, containing hydrogen peroxide, after reconcentration by the removal of water by distillation, into the reaction, which is characterised in that the raffinate is fed, together with the whole amount of hydrogen peroxide which essentially corresponds to the consumption of hydrogen peroxide in the reaction or with a part thereof, into the distillation for the removal of water and that the amount of water which essentially corresponds to the sum of the water of reaction formed during the reaction and the water introduced into the process with the feed products is then distilled off under reduced pressure and the sump product, thus obtainable, from the distillation is recycled into the reaction.

Surprisingly, a quite considerable increase in the yield of percarboxylic acid is achieved by the simple measure of feeding fresh hydrogen peroxide, which is required for the reaction of aqueous hydrogen peroxide with the carboxylic acid and which is to be added continuously, together with the raffinate from the extraction into the distillation which serves to remove water, and recycling the sump product obtained from the distillation into the reaction with the carboxylic acid. In general, the yield of percarboxylic acid in the process according to the invention is more than 95%, for example about 97%, relative to the hydrogen peroxide fed into the process.

Suitable carboxylic acids for the process according to the invention are aliphatic, cycloaliphatic and aromatic carboxylic acids. The appropriate carboxylic acids can contain up to 20, preferably up to 8, carbon atoms. The carboxylic acids can be substituted by fluorine or chlorine.

Examples of aliphatic carboxylic acids which can be used are formic acid, acetic acid, propionic acid, butyric acid, isobutyric acid, valeric acid, trimethylacetic acid, caproic acid, heptylic acid, caprylic acid, pelargonic acid, capric acid, undecanoic acid, lauric acid, myristic acid, pentadecanoic acid, palmitic acid, stearic acid, arachic acid, fluoroacetic acid, trifluoroacetic acid, chloroacetic acid, dichloroacetic acid, trichloroacetic acid, α-chloropropionic acid, α-fluoropropionic acid, β-chloropropionic acid, succinic acid, glutaric acid, adipic acid, suberic acid, azelaic acid and sebacic acid. Cycloaliphatic carboxylic acids which may be mentioned are cyclopentanecarboxylic acid, cyclohexanecarboxylic acid, cycloheptanecarboxylic acid, cyclohexane-1,3-dicarboxylic acid and cyclohexane-1,4-dicarboxylic acid. Aromatic carboxylic acids which can be used are benzoic acid, p-chlorobenzoic acid, phthalic acid, naphthalenecarboxylic acid, benzene-1,3-dicarboxylic acid and benzene-1,4-dicarboxylic acid.

Aliphatic carboxylic acids with 1 to 4 carbon atoms, such as formic acid, acetic acid, propionic acid, n-butyric acid and isobutyric acid, are particularly suitable for the process according to the invention. Propionic acid is very particularly suitable.

Acid, water-soluble catalysts which can be used are sulphuric acid and acid salts of sulphuric acid, as well as phosphoric acid, sulphonic acids, chlorinated or fluorinated sulphonic acids or mixtures of these acid catalysts. Catalysts which may be mentioned individually are sulphuric acid, sodium bisulphate, potassium bisulphate, methanesulphonic acid, ethanesulphonic acid, propanesulphonic acid, butanesulphonic acid, isobutanesulphonic acid, benzenesulphonic acid, toluenesulphonic acid, trifluoromethanesulphonic acid, 1-fluoromethanesulphonic acid, perfluoroethanesulphonic acid, perfluoropropanesulphonic acid and perfluorobutanesulphonic acid. Sulphuric acid is preferably used. Of course, it can be appropriate, for example when less readily water-soluble carboxylic acids, such as the long chain acids of the lauric acid type, are employed, to use the catalyst in larger amounts. This can be the case in particular when the acid catalyst, for example concentrated sulphuric acid, is at the same time intended to serve as the solvent (see also D. Swern "Organic Peroxides", Wiley Interscience 1971, volume 1, page 484).

Suitable extraction agents for the percarboxylic acids are all solvents which are not miscible with water and which are virtually inert towards hydrogen peroxide, the percarboxylic acid and the acid catalyst. For example, aliphatic, cycloaliphatic and aromatic hydrocarbons, chlorinated hydrocarbons as well as esters of carboxylic acids and ethers are suitable. The number of carbon atoms in these solvent compounds is generally 1 to 20, preferably 2 to 10. Suitable extraction agents are, for example, n-pentane, isooctane, cyclohexane, benzene, toluene, xylene, methylene chloride, chloroform, 1,2-dichloroethane, 1,2-dichloropropane, methyl acetate, ethyl acetate, n-propyl acetate, isopropyl acetate, n-butyl acetate, isoamyl acetate, methyl propionate, ethyl propionate, propyl propionate and butyl propionate, diethyl ether, di-t-butyl ether as well as chlorobenzene. Chlorinated hydrocarbons, such as methylene chloride or dichloroethane, and aromatic hydrocarbons are preferably used. Benzene is preferentially used as the extraction agent for the process according to the invention.

The feed molar ratio of aqueous hydrogen peroxide to carboxylic acid can be varied within wide limits. For example, the ratio of hydrogen peroxide to carboxylic acid is 0.5 to 30:1. The molar ratio of hydrogen peroxide to carboxylic acid which is selected for the reaction is preferably from 0.8 to 1.5:1, preferentially from 0.9 to 1.3:1. The concentration of the aqueous hydrogen peroxide used is generally less than 60% by weight. The reaction temperature is generally 10° to 70° C. Approximately, the reaction is carried out below 60° C. Temperatures below 45° C are particularly advantageous for the reaction. It is very particularly appropriate to maintain reaction temperatures of 30° to 40° C. The pressure is not important for the reaction of the carboxylic acid with hydrogen peroxide, so the reaction can be carried out at normal pressure, elevated pressures or at reduced pressure. In generaly it is appropriate to work at pressures below 1.1 bars. In general, the reaction of the carboxylic acid with hydrogen peroxide is carried on until the equilibrium between percarboxylic acid and carboxylic acid is set up. However, it is also possible to discontinue the reaction before equilibrium is reached and to feed the reaction mixture thus obtained to the extraction with the organic solvent. The extraction of the reaction mixture from the reaction of carboxylic acid and hydrogen peroxide is generally carried out in such a way that percarboxylic acid and carboxylic acid are extracted as completely as possible, so that the raffinate virtually contains all the unreacted hydrogen peroxide and the water-soluble acid catalyst. However, it is also possible to carry out the extraction less completely and to further work up the resulting raffinate according to the invention.

The raffinate is reconcentrated by distilling the entire raffinate or part of the raffinate in a manner which is in itself known for example according to the process of DOS (German Published Specification) No. 2,262,970. Prior to the distillation, hydrogen peroxide is added to the raffinate. The raffinate is distilled with fresh hydrogen peroxide, so that a reconcentration of the mixture is effected by distilling off the water. In general, the procedure is such that the raffinate is fed, with addition of aqueous $H_2O_2$ solution to make up the hydrogen peroxide consumed in the reaction with carboxylic acid, into the distillation column used for reconcentration. The raffinate and the hydrogen peroxide are mixed with one another in the appropriate ratio, for example before feeding into the distillation unit. However, it is also possible to feed the raffinate and the aqueous $H_2O_2$ in the appropriate ratio directly into the distillation unit. It is possible to feed the raffinate and the aqueous $H_2O_2$ into the distillation unit at different points or to feed them to the column at the same point. Preferably, the mass flows are fed into the distillation column at the point at which the concentration conditions in the column are closest to the concentration at the inlet.

It is likewise possible to add the fresh hydrogen peroxide partly to the aqueous raffinate of the extraction after reconcentration.

Thus, a substantial part of the fresh hydrogen peroxide, which is required in the process, e.g. 50% by weight of this amount, can be added to the raffinate prior to the removal of water by distillation and the remaining 50% by weight of the fresh hydrogen peroxide added to the concentrated raffinate stream.

The process is preferably carried out in such a manner that 50 to 75% by weight of the fresh hydrogen peroxide is added to the raffinate of the extraction prior to concentration, whilst the remaining 25 to 50% by weight of the amount of the fresh hydrogen peroxide needed in the process is added to the raffinate after concentration. It is possible to mix the part of fresh hydrogen peroxide to be added prior to the raffinate concentration with the raffinate before entry into the distillation unit or to introduce both streams separately at a suitable place into the distillation unit. The amount of fresh hydrogen peroxide, which is added to the raffinate not prior to concentration, can also be introduced directly into the reaction with propionic acid.

In this case, as in the case of the addition of a part of the fresh hydrogen peroxide to the concentrated raffinate, the concentration of $H_2O_2$ and acid catalyst must be correspondingly altered in the concentrated raffinate (in so far as the partial streams of fresh hydrogen peroxide which are used in the process as aqueous solutions have the same concentrations).

This alteration to the concentrate must be carried out in order that the required amount ratio of $H_2O_2$, acid catalyst and water be kept to for the reaction with propionic acid. This is expediently carried out in such a manner that the amount of water, which is introduced into the process with the partial stream of the fresh hydrogen peroxide added to the raffinate after concentration or directly to the reaction with propionic acid is removed by distillation: this is preferably achieved in the distillation unit used for the concentration of the raffinate.

It is also possible, however, to introduce partial streams of fresh hydrogen peroxide into the process which have a varying concentration of $H_2O_2$. Thus, it is possible, for example, to add 70% by weight of the required amount of fresh hydrogen peroxide to the raffinate of the extraction prior to concentration in the form of a 50% by weight aqueous solution, whilst the remaining 30% by weight of fresh hydrogen peroxide are introduced as a more highly concentrated aqueous solution of $H_2O_2$, for example, as a 70% by weight solution.

In a preferred embodiment of the process, the process is carried in such a way that the amount of fresh $H_2O_2$, which is added to the raffinate of the extraction prior to removal of water by distillation, amounts to 75 to 95% by weight of the total amount of fresh hydrogen peroxide and that the remaining 5 to 25% by weight of fresh $H_2O_2$ is added to the concentrated raffinate. In a particularly preferred embodiment, the process is so performed that the fresh hydrogen peroxide is introduced by adding the total amount to the raffinate of the extraction prior to concentration in a distillation unit.

In general, a distillation column which is provided with an evaporator unit is used to reconcentrate the raffinate. The customary columns can be used as the distillation column. For example, packed columns or trayed columns are suitable. Customary equipment, such as circulation reboilers, falling flow evaporators or thin layer evaporators, are also suitable as the evaporator. Preferably, a falling flow evaporator or a thin layer evaporator is used.

The aqueous hydrogen peroxide, which passes with the raffinate into the distillation column, is generally a commercially available hydrogen peroxide. The concentration of the hydrogen peroxide is not important for the process of the invention. In general, $H_2O_2$ in a concentration of from 5 to 90%, preferably from 30 to 75%, is used. Stabilisers can be added to the aqueous hydrogen peroxide. For example, stabilisers such as are mentioned in "Gmelins Handbuch der anorganischen Chemie" (Gmelins Handbook of Inorganic Chemistry), 8th edition, oxygen volume, section 7, 1966, page 2,274 and 2,275 can be used.

The distillation is usually carried out under reduced pressure. It is appropriate to work at pressures of from 10 to 250 mm Hg. In many cases it is particularly advantageous to use pressures of from 50 to 150 mm Hg. The temperature in the evaporator of course depends on the composition of the sump products and on the pressure; it is, for example, 40° to 120° C, preferably 60° to 85° C. In general, the conditions are so selected that the sump temperature is lower than 85°, preferably lower than 80° C.

The water obtained from the distillation can contain small amounts of hydrogen peroxide. In general, the hydrogen peroxide content in the aqueous distillate can be adjusted to less than 0.2% by weight without difficulty. However, it is also possible to control the distillation in such a way that the distillate contains less than 0.1% by weight of $H_2O_2$. Of course, constituents which are volatile with steam and are contained in the raffinate can pass into the distillate. Thus, for example, small amounts of percarboxylic acid or carboxylic acid which have not been extracted can pass over, with the water, into the distillate. In general, the aqueous distillate contains less than 2% by weight of percarboxylic acid and less than 1% by weight of carboxylic acid.

Suitable materials for the distillation unit are glass, enamelled steels, teflon-lined steels and high grade stainless steels which, in addition to iron, in the main also contain chromium and nickel. Tantalum or zirconium can be used. Examples of high-grade stainless steels which may be mentioned are a material with the DIN designation 1.4571, which, in addition to iron, contains 17.5% by weight of chromium, 11.5% by weight of nickel, 2.25% by weight of molybdenum and also up to 2% by weight of manganese, up to 1% by weight of silicon, up to 0.1% by weight of carbon and small amounts of titanium, or a material which, in addition to iron, contains 25% by weight of chromium, 25% by weight of nickel, 2.25% by weight of molybdenum and up to 2% by weight of manganese, up to 1% by weight of silicon, up to 0.06% by weight of carbon and also small amounts of titanium and which is designated according to DIN by the number 1.4577.

Zirconium or the high grade steel with the material designation DIN 1.4577 are particularly suitable. Other materials, for example aluminium, can also be used for those parts of the distillation column which do not come into contact with the acid catalyst.

The concentration of hydrogen peroxide in the raffinate can vary within wide limits. The raffinate generally contains 5 to 25, usually 6 to 15, % by weight of hydrogen peroxide. The concentration of the acid catalyst in the raffinate depends on the nature of the acid catalyst. The concentration of acid catalyst in the raffinate is generally 10 to 50, usually 12 to 40, % by weight.

After reconcentration of the raffinate, an aqueous solution which contains about 20 to 40% by weight of hydrogen peroxide and about 15 to 45% by weight of acid catalyst is generally obtained. These concentrations can also be higher or lower than stated.

In an industrial embodiment of the process according to the invention, an aqueous solution containing 25 to 35% by weight of hydrogen peroxide and 25 to 40% by weight of sulphuric acid is reacted with propionic acid at a molar ratio of hydrogen peroxide to propionic acid of 0.8 up to 1.5:1. The equilibrium mixture formed is extracted with benzene. A benzene solution containing 15 to 25% by weight of perpropionic acid is obtained as the extract. The raffinate contains 8 to 15% by weight of hydrogen peroxide, 30 to 45% by weight of sulphuric acid, less than 0.2% by weight of perpropionic acid and less than 0.2% by weight of propionic acid.

The raffinate is fed, together with the amount of commercially available 50% strength aqueous hydrogen peroxide which corresponds to the consumption of $H_2O_2$ in the conversion of propionic acid to perpropionic acid, into a distillation unit. The distillation unit consists of a bubble cap tray column and a falling film evaporator. At a pressure below 150 mm Hg, water is distilled off continuously over the top, at an evaporator temperature of 50° to 90° C, in the same amount as passes continuously, in the form of the 50% strength aqueous hydrogen peroxide, into the column and as is formed during the reaction of hydrogen peroxide with propionic acid. The composition of the sump product from the distillation column is about 25 to 35% by weight of hydrogen peroxide and 25 to 40% by weight of sulphuric acid; the remainder is water. Part of the hydrogen peroxide and sulphuric acid can also form Caro's acid. For example, Caro's acid can be present in concentrations of from 1 to 10% by weight. The distillate contains less than 0.1% by weight of hydrogen peroxide and about 0.5% by weight of perpropionic acid. The yield of perpropionic acid in benzene solution, relative to the hydrogen peroxide employed in the process, is more than 95%.

It must be regarded as extremely surprising that such a high final yield of percarboxylic acid can be achieved when, according to the process of the invention, the amount of fresh hydrogen peroxide required for the continuous reaction of carboxylic acid with hydrogen peroxide is not entirely added in the reaction stage itself, but is added in a whole or in part while the raffinate is being worked up, by distillation, in order to recycle the unreacted hydrogen peroxide and the acid catalyst contained in the raffinate.

EXAMPLE 1

The equipment set consists of a reaction system, an extraction system and a distillation unit. A delay tube which is 50 cm in length and 5 cm in diameter and which is provided with packing serves as the reaction system. The extraction system comprises a pulsed sieve tray column which is 4 m in length and 2.5 cm in diameter and which is provided with 80 trays. The distillation unit consists of a bubble cap tray column which is 1 m in length and 5 cm in diameter and which is provided with a falling film evaporator.

619 g per hour of an aqueous solution, which contains 32.8% by weight of sulphuric acid, 29.1% by weight of hydrogen peroxide and 5.8% by weight of Caro's acid and which is withdrawn as the sump product from the distillation unit, as well as 415 g per hour (5.6 mols) of propionic acid are fed continuously to the reaction system. The molar ratio of hydrogen peroxide to propionic acid in the mixture which passes into the reaction system is 1:1, the hydrogen peroxide contained in the Caro's acid being calculated as free $H_2O_2$. This mixture is warmed to 38° C for 20 minutes in the delay tube which serves as the reaction system and 59% of the propionic acid fed in is converted to perpropionic acid. A product stream, cooled to 20° C, is obtained, in an amount of 1,034 g per hour, after the delay tube and has the following composition: 28.8% by weight of perpropionic acid, 16.46% by weight of propionic acid, 19.6% by weight of $H_2SO_4$, 3.47% by weight of Caro's acid, 6.54% by weight of $H_2O_2$ and 25.13% by weight of water. This product stream is fed to the extraction system and extracted in the sieve tray column with benzene in counter-current at a temperature of 20° C, the aqueous solution containing perpropionic acid being fed into the extraction column at the upper end and the benzene used as the extraction agent being fed, in an amount of 961 g per hour, into the lower part of the column. 1,439 g per hour of a 20.67% strength by weight benzene solution of perpropionic acid, which also still contains 11.78% by weight of propionic acid as well as 0.69% by weight of water and 0.07% by weight of hydrogen peroxide, are obtained as the extract. The aqueous solution, which contains 36.5% by weight of sulphuric acid, 11.98% by weight of hydrogen peroxide and 6.45% by weight of Caro's acid as well as 0.1% by weight of propionic acid and 0.07% by weight of perpropionic acid, which is obtained as the raffinate and which is withdrawn, in an amount of 556 g per hour, from the extraction column, is fed to the distillation unit, this mixture being combined with 194 ml per hour of a 50% strength by weight aqueous solution of hydrogen peroxide ($\triangleq$115.9 g of $H_2O_2$ = 3.408 mols). The distillation column is operated at a pressure of 50 mm Hg. At a sump temperature of 65° C, a top temperature of 35° C and a reflux ratio of 0.5, 168 ml per hour of water are distilled off. The distillate contains 0.23% by weight of perpropionic acid and 0.35% by weight of propionic acid as well as traces of hydrogen peroxide. 619 g per hour of an aqueous solution, which contains the sulphuric acid, Caro's acid and hydrogen peroxide in the composition already mentioned above, are withdrawn from the sump of the distillation column and recycled, together with propionic acid, into the reaction system.

The yield of perpropionic acid in the benzene extract is 96.95%, relative to the amount of hydrogen peroxide charged into the process.

EXAMPLE 2 (COMPARISON EXAMPLE)

The process is carried out in the same equipment as described in Example 1. The same mass flows, having the compositions mentioned in Example 1, are fed per hour into the reaction system and extraction system. 1,439 g per hour of a 20.67% strength by weight benzene solution of perpropionic acid, which also still contains 11.78% by weight of propionic acid, 0.69% of water and 0.07% of hydrogen peroxide, are again obtained as the extract. 556 g per hour of an aqueous solution which has the following composition: 36.5% by weight of sulphuric acid, 11.98% by weight of hydrogen peroxide, 6.45% by weight of Caro's acid as well as 0.07% by weight of perpropionic acid and 0.1% by weight of propionic acid, are also again obtained as the raffinate from the extraction. This raffinate is now fed direct, without previously having been combined with the hydrogen peroxide to be employed in the process, into the distillation column of Example 1, which is operated at a pressure of 50 mm Hg, and 185 ml per hour of water, which contains 0.21% by weight of perpropionic acid and 0.32% by weight of propionic acid, are taken off as the top product. A solution which contains 9.84% by weight of Caro's acid, 55.62% by weight of sulphuric acid, 14.52% by weight of hydrogen peroxide and also 20% by weight of water is withdrawn from the sump of the column in an amount of 365 g per hour. This solution is cooled to room temperature and then treated with 213 ml per hour of a 50% strength by weight aqueous solution of hydrogen peroxide ($\triangleq$127.1 g of $H_2O_2 \triangleq$ 3.74 mols), after which the resulting mixture (619 g/hour, which now again contains 5.8% by weight of Caro's acid, 32.8% by weight of sulphuric acid, 29.1% by weight of hydrogen peroxide and 32.3% by weight of water, is recycled, together with 415 g per hour of propionic acid, into the reaction system. The yield of perpropionic acid in the benzene extract (297.4 g/hour ≙ 3.304 mols/hour) is only 88.38%, relative to the hydrogen peroxide charged per hour.

We claim:

1. In the process for the continuous production of an organic solution of percarboxylic acid which comprises contacting aqueous hydrogen peroxide with the corresponding carboxylic acid for the reaction of the hydrogen peroxide and carboxylic acid to form the percarboxylic acid and water in an reaction mixture, in the presence of an acid, water soluble catalyst for the reaction, extracting the reaction mixture with organic solvent selected from the group consisting of aliphatic, cycloaliphatic and aromatic hydrocarbons, chlorinated hydrocarbons, esters of carboxylic acids and ethers to form a solvent phase rich in the carboxylic acid and an aqueous raffinate phase rich in hydrogen peroxide and catalyst, distilling the raffinate to remove water therefrom and form a concentrated aqueous, hydrogen peroxide, acid solution and recycling the concentrated solution, said contacting, wherein aqueous make-up hydrogen peroxide and make-up carboxylic acid are introduced into said contacting to replace hydrogen peroxide and carboxylic acid consumed in the reaction, the improvement which comprises introducing at least part of the make-up aqueous hydrogen peroxide into said distillation for distillation thereof together with distillation of the raffinate, the amount of water removed in the distillation being about equal to the sum of the water formed in the reaction and the water introduced into the process, said distillation being performed at 10-250 mm Hg. and 40°-120° C to provide the distilled water as overhead and said concentrated solutions as sump product, and recycling the sump product to said contacting.

2. Process of claim 1, wherein the carboxylic acid contains 1 – 4 carbon atoms.

3. Process of claim 1, wherein the carboxylic acid is propionic acid.

4. Process of claim 1, wherein the catalyst is sulfuric acid.

5. Process of claim 1, wherein, in said contacting, the ratio of hydrogen peroxide : carboxylic acid is 0.5–30:1.

6. Process of claim 1, wherein, in said contacting, the temperature is 10° – 70° C.

7. Process of claim 1, wherein said organic solvent is a chlorinated hydrocarbon.

8. Process of claim 1, wherein said organic solvent is an aromatic hydrocarbon.

9. Process of claim 1, wherein said organic solvent is benzene.

10. Process of claim 1, wherein the make-up aqueous hydrogen peroxide introduced into said distillation is 30 – 75% aqueous hydrogen peroxide.

11. Process of claim 1, wherein said distillation is performed at 10 – 250 mm Hg.

12. Process of claim 1, wherein the distillation is performed at a temperature of 60° – 85° C.

13. Process of claim 1, wherein the distillation is performed at a pressure of less than 150 mm Hg.

14. Process of claim 1, wherein the distillation is performed with the aid of a thin layer evaporator or a falling film evaporator.

15. Process of claim 1, wherein the water distilled off in said distillation contains less than 0.1 wt.% of hydrogen peroxide.

16. Process of claim 1, wherein the amount of make-up hydrogen peroxide introduced into said distillation is at least 50% by weight of the hydrogen peroxide consumed in said reaction.

17. Process of claim 1, wherein the amount of make-up hydrogen peroxide introduced into said distillation is 50 – 70% by weight of the hydrogen peroxide consumed in said reaction.

18. Process of claim 1, wherein the amount of make-up hydrogen peroxide introduced into said distillation is 75 – 95% by weight of the hydrogen peroxide consumed in said reaction.

19. Process of claim 1, wherein the amount of make-up hydrogen peroxide introduced into said distillation is 100% by weight of the hydrogen peroxide consumed in said reaction.

20. Process of claim 1, wherein, in said contacting, the carboxylic acid is propionic acid, the acid catalyst is sulfuric acid, the ratio of hydrogen peroxide : carboxylic acid is 0.5 – 30:1, and the temperature is 10° – 70° C; and, in said extraction, the organic solvent is benzene; and in said distillation, the temperature is 60° – 85° C.

21. Process of claim 1, wherein the amount of make-up hydrogen peroxide introduced into said distillation is at least 50% by weight of the hydrogen peroxide consumed in said reaction.

22. Process of claim 20, wherein the amount of make-up hydrogen peroxide introduced into said distillation is 50 – 70% by weight of the hydrogen peroxide consumed in said reaction.

23. Process of claim 20, wherein the amount of make-up hydrogen peroxide introduced into said distillation is 75–95% by weight of the hydrogen peroxide consumed in said reaction.

24. Process of claim 20, wherein the amount of make-up hydrogen peroxide introduced into said distillation is 100% by weight of the hydrogen peroxide consumed in said reaction.

25. Process of claim 1, wherein the yield of percarboxylic acid is more than 95% based on the hydrogen peroxide fed to the process.

26. Process of claim 1, wherein the catalyst is sulphuric acid, acid salt of sulphuric acid, phosphoric acid, a sulphonic acid, chlorinated sulphonic acid, fluorinated and sulphonic acid and or a mixture thereof.

27. Process of claim 26 wherein the carboxylic acid is propionic acid.

28. Process of claim 27, wherein the solvent is not miscible with water and is virtually inert towards hydrogen peroxide, the percarboxylic acid and the acid catalyst.

* * * * *